(12) United States Patent
Nguyen et al.

(10) Patent No.: US 8,568,703 B2
(45) Date of Patent: *Oct. 29, 2013

(54) AEROSOL ODOR ELIMINATING COMPOSITIONS CONTAINING ALKYLENE GLYCOL(S)

(75) Inventors: Peter N. Nguyen, Racine, WI (US); Bhaveshkumar Shah, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/609,640

(22) Filed: Sep. 11, 2012

(65) Prior Publication Data
US 2013/0001260 A1     Jan. 3, 2013

Related U.S. Application Data

(63) Continuation of application No. 12/801,640, filed on Jun. 18, 2010, now Pat. No. 8,287,841.

(51) Int. Cl.
*A61L 9/012*     (2006.01)

(52) U.S. Cl.
USPC ............ 424/76.6; 424/45; 510/594; 510/504; 510/278; 510/276

(58) Field of Classification Search
USPC ............ 424/76.6, 45; 510/594, 504, 278, 276
See application file for complete search history.

(56) References Cited

U.S. PATENT DOCUMENTS

| | | | | |
|---|---|---|---|---|
| 6,303,111 | B1 * | 10/2001 | Maurer et al. | 424/76.1 |
| 7,448,517 | B2 * | 11/2008 | Shieh et al. | 222/394 |
| 2006/0292111 | A1 * | 12/2006 | Valpey et al. | 424/76.2 |
| 2007/0142264 | A1 * | 6/2007 | Nguyen et al. | 510/504 |
| 2008/0069780 | A1 * | 3/2008 | Weiss et al. | 424/45 |
| 2009/0020621 | A1 * | 1/2009 | Clark et al. | 239/8 |

OTHER PUBLICATIONS

DOW Technical Data Sheet for TERGITOL 15-s-7 Surfactant.*

\* cited by examiner

*Primary Examiner* — Anoop Singh
*Assistant Examiner* — Anna Falkowitz

(57) ABSTRACT

Aerosol odor eliminating compositions are described which are aqueous based and include at least one alkylene glycol, at least one surfactant wherein one or more of the at least one surfactant has an HLB of about 7 to about 20, compressed gas propellant, at least one fragrance, a buffering system and water. The composition excludes inclusion of a low molecular weight monohydric. The compositions have a volatile organic content (VOC) of less than 5.0% of the total composition based on 100 wt. %, or alternatively, a VOC of less than 0.1% as to the total composition based on 100 wt. % in absence of the wt. % of the active fragrant material of the fragrance. The compositions additionally have a consistent spray rate at multiple pressure ranges.

20 Claims, 3 Drawing Sheets

Average spray down rates of Glencoe caps on samples pressurized to 170, 160 and 150 PSIG

AEROSOL ODOR ELIMINATING COMPOSITIONS CONTAINING ALKYLENE GLYCOL(S)

RELATED APPLICATION

This application is a continuation of U.S. Ser. No. 12/801,640 filed Jun. 18, 2010, now U.S. Pat. No. 8,287,841 B2.

FIELD OF INVENTION

Aerosol compositions are provided for eliminating airborne malodors. The compositions are aqueous-based and include compressed gas, fragrance and a solubilizing system for at least the fragrance. The compositions have a low to almost zero volatile organic content (VOC).

BACKGROUND OF THE INVENTION

A wide variety of deodorizing compositions are known in the art, the most common of which contain perfumes or fragrances to mask malodors. Odor masking is the intentional concealment of one odor by the addition of another. In order to mask odors using perfumes or fragrances, however, high levels of fragrance are generally needed to ensure that the malodor is no longer noticeable or suitably masked and the masking techniques do nothing to remove or modify the source of the odor. Aerosol spray air sanitizers are known in the art to effectively kill airborne microorganisms and mitigate airborne malodorants. The active ingredients in currently available aerosol air sanitizers vary. One family of products relies upon glycols, such as propylene glycol, dipropylene glycol and triethylene glycol. The most popular is triethylene glycol, the active ingredient in the OUST® family of products sold by S. C. Johnson & Son, Inc. Triethylene glycol (TEG) is known to kill certain airborne bacteria. TEG is also safe for use in aerosol sprays. Because the solubility of TEG in conventional hydrocarbon propellants is generally low, additional solvents, such as ethanol, are added to TEG-based aerosol compositions to increase the solubility of TEG in hydrocarbon propellants. Ethanol is also used as a co-solvent to increase volatility of the product and to make other components, such as fragrance oils, more soluble.

However, the use of ethanol and other conventional solvents in combination with conventional short C-chain aliphatic propellants limits the amount of TEG that can be included in a single-phase formulation. For example, the concentration of TEG in a single-phase aerosol composition using conventional hydrocarbon propellant is limited to no more than 6-8 wt. % with 30 wt. % propellant and the rest being ethanol. The use of TEG in amounts that exceed 12 or 15 wt. % normally results in a two-phase system, thereby requiring the consumer to vigorously shake the canister before use and foreclosing use of the formulation in a continuous or automated spray device. Single-phase aerosol products that do not require vigorous shaking are advantageous because consumers often forget to shake multi-phase products that require mixing and, because the performance of single-phase aerosol products is not dependent upon mixing, the performance of single-phase aerosols can be more consistent. In contrast, the efficacy of multi-phase aerosol products that require mixing can be somewhat inconsistent, especially if the user is physically unable to shake the can as vigorously as required.

Both ethanol and hydrocarbon propellants are considered to be volatile organic compounds. The content of volatile organic compounds in aerosol air sanitizers has the potential to be regulated by federal and/or state regulatory agencies, such as the Environmental Protection Agency (EPA) and California Air Resource Board (CARB). An existing single-phase TEG-based aerosol composition typically has a volatile organic compound content of more than 90 wt. %. By increasing the content of TEG, the volatile organic compound content of the aerosol composition can be reduced as well.

SUMMARY OF THE INVENTION

Aerosol odor eliminating compositions are provided. The aerosol compositions are aqueous based and include at least one alkylene glycol, at least one surfactant, compressed gas propellant, at least one fragrance, and buffering system. The alkylene glycol and/or surfactant serve to solubilize the fragrance and other component(s) which may be present requiring solubilization, e.g. preservative. The aerosol odor eliminating compositions do not contain a low molecular weight monohydric alcohol. The compositions have a low to almost zero volatile organic content (VOC). Further, the compositions have a good and substantially consistent spray rate over a pressure range of 130-180 psig at room temperature, it being understood that this pressure refers to the initial pressure in a container. The pressure will drop at a linear rate over the life of the product. However, the compositions of the invention have a substantially consistent particle size and spray rate for at least about 70 to 75% of the life of the aerosol in the container. Pressure drop occurs during the life of aerosols due to the changing headspace in the container. Consistency in particle size and spray rate over a substantial period of the life of the aerosol is therefore advantageous.

Further advantages of the aerosol odor eliminating compositions include that the compositions are water based, as opposed to solvent based (e.g. alcohol containing), and yet provide solubilization of one or more fragrances contained in the compositions resulting in single phase compositions. The compositions do not have an oily-feeling fall-out onto surfaces and provide a uniform mixture resulting in a consistent or substantially consistent spray rate over a wide pressure range for good dispersion of the active ingredients in the compositions.

Further, the aerosol compositions have a volatile organic content (VOC) of less than 5.0% as to the total composition based on 100 wt. %, preferably less than 3.0% as to the total composition, most preferably less than 1.0%; and further less than 0.5%; or, alternatively expressed, the aerosol compositions have a VOC of less than 0.1% of the total composition based on 100 wt. % in the absence of the active fragrance content based on wt. %, preferably less than 0.05%, and most preferably less than 0.01% in the absence of fragrance content. The VOC is provided at a low to almost zero amount based on primarily the absence of need for alcohol as a solvent and hydrocarbons as propellant.

The buffering system of the aerosol compositions provided is preferably based on citric acid and/or a citrate compound, i.e., the buffering system is citric acid alone, a citrate compound (e.g. an alkali metal citrate) alone, or a combination of citric acid and a citrate compound. Further, useful in themselves or includable with any of the above buffering systems is a phosphate buffer compound, such as an alkali metal hydrogen phosphate, such as dipotassium hydrogen phosphate and potassium dihydrogen phosphate, or another buffer component such as an alkali metal hydroxide or alkali metal bicarbonate, for example, sodium hydroxide or sodium bicarbonate. A buffering system containing only the citric acid and/or the citrate compound is in particular advantageous as not containing a phosphorous-containing component, such are not being available for use in all geographic locations based on present or potential state or country regulations. The aqueous-based compositions as described herein, therefore, provide a combination which can be adequately buffered without the need for inclusion of a phosphorous-containing compound. Other advantages of the citric acid and/or citrate buffering system include that such does not result in any color change to the overall composition when incorporated therein and is stable for an extended period of time which provides for an extended shelf and storage life.

The novel features and benefits of the aerosol odor eliminating compositions will be further appreciated in view of the detailed description below.

DETAILED DESCRIPTION OF THE INVENTION

Figure 1:
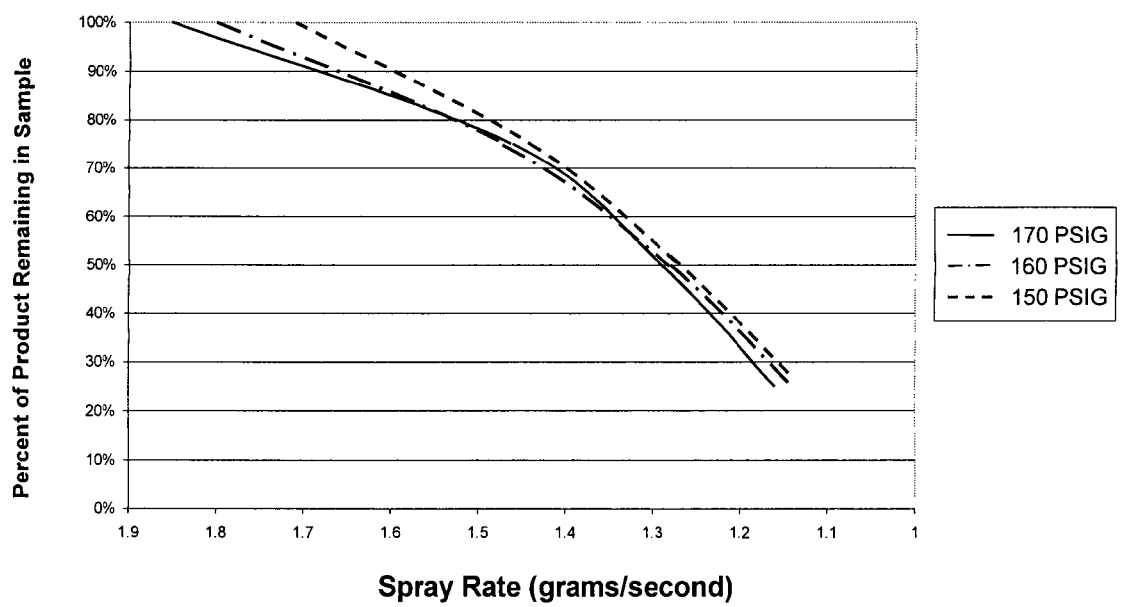
FIG. 1 shows graphically the average spray rate for samples evaluated at 170, 160 and 150 psig.

The aerosol odor eliminating compositions provided herein include (a) at least one alkylene glycol, (b) at least one surfactant, (c) compressed gas propellant present at a maximum of approximately 180 psig at room temperature, (d) a buffering system, (e) at least one fragrance, and (f) water. The composition does not include any low molecular weight monohydric alcohol. The composition has a volatile organic content (VOC) of less than 5.0% for the total composition based on 100 wt. % or, alternatively, a VOC of less than 0.1% for the total composition based on 100 wt. % in the absence of the at least one fragrance based on the wt. % of the active fragrance material therein. The fragrance is solubilized by the surfactant, or the alkylene glycol, or a combination of the surfactant and the alkylene glycol. The pH of the composition is about 4 to about 8, preferably about 5 to about 7.

Elimination of odor(s) in the air is provided using the aqueous-based aerosol composition containing at least one alkylene glycol, such as triethylene glycol or propylene glycol. Additional odor elimination properties can be attributed to other composition components present, such as the surfactant system, a pH buffering system and the fragrance compounds.

Alkylene glycols in aerosol air compositions fight malodors. The mechanism of odor elimination by which an aerosol droplet containing alkylene glycols interacts with odor molecules first involve solubilization of the malodors followed by "rain out" of the aerosol droplet. Thereafter, chemical and physical reactions between the malodors, and the surfactants, fragrances and pH stabilized liquid droplet can take place.

As the aerosol product is sprayed, a fine mist of liquid droplets is dispersed in the air. The dispersed liquid droplets, which have a significant surface area, begin to solubilize the malodor compounds present in the air. This initial removal of the odor molecule is governed by gas/liquid partitioning. The partitioning is an equilibrium process in which odors in the gas phase migrate into the liquid droplet to establish an equilibrium governed by the partitioning coefficient of the system. This process can be described using Henry's Law which defines an equilibrium constant as a ratio of the amount of gas dissolved in a given liquid and the partial pressure of that gas in the gas phase, as in the following equation:

$$K = \frac{p}{c}$$

where K is the equilibrium constant known as the Henry's Law constant, p is the partial pressure of the odor above the solution and c is the concentration of the odor in the solution.

As the gas/particle partitioning is taking place, the aerosol particles begin to settle out of the air. This settling process, referred to as "raining out", occurs as the liquid droplets begin to fall out of the air. This raining out process carries along the malodors already absorbed into or adsorbed onto the droplets, thereby removing them from the air.

Once the odor molecules are absorbed into the liquid droplets, one of several secondary mechanisms can further interact with the malodor, to limit its ability to re-release from the aerosol droplets. The secondary processes of odor elimination can involve the solubilization of the malodor by the surfactant system, neutralization through acid-base chemistry, and/or chemical interaction with fragrance molecules.

The presence of a surfactant system in the aerosol composition can lead to the formation of self-assembled surfactant structures as a thin film on the aerosol droplet or as micellar structures within the aerosol droplet. These surfactant structures are typically used to solubilize the fragrance into the liquid droplet but can also interact with the malodor molecules which have partitioned into the droplet. This interaction can lead to the solubilization of malodors either from within the liquid droplet or at the surface/air interface. The solubilization of the odors by self-assembled structures can lead to a reduction in the gas phase concentration of the malodor, resulting in further odor elimination.

The aerosol system has a pH of about 4 to about 8, which is achieved using a buffering system. The buffered solution in the aerosol particles can interact with the solubilized malodors through an acid-base chemistry to further neutralize the odors. For example, an amine malodor such as ammonia which is solubilized by the aerosol particle can have a portion of the free amine ionized to the ammonium ion due to the presence of the buffering system. The ammonium ion can then form ammonium phosphate, in the event of a phosphate-based buffering system, which has a vapor pressure significantly less than the free amine and therefore is less likely to re-release from the particle.

The presence of fragrance molecules solubilized in the aerosol droplet with the malodor molecules can lead to interactions between the two molecules. It is widely known that some common fragrance components are able to interact with malodor molecules leading to the formation of less offensive odors. This interaction may occur in the droplet after the malodor is absorbed or by the fragrance molecules released from the aerosol during use.

The overall mechanism for odor elimination is the solubilization of the odor molecules into the aerosol droplet followed by the "raining out" of the aerosol particles from the air. The solubilized odor can then be further removed by one or more of the secondary processes which includes: secondary solubilization by the surfactant system, neutralization by acid-base chemistry and/or the chemical interaction with fragrance molecules.

As to the alkylene glycol component of the aerosol odor elimination composition, the at least one alkylene glycol is included in an amount of about 0.1 to about 10 wt. % of the composition, preferably about 0.1 to about 5 wt. %, and most preferably about 0.5 to about 1.5 wt. %. The alkylene glycol component serves to eliminate odor in an environment to which the composition is applied in use, as well as serves as a component of the solubilizing system of the composition, e.g. for solubilizing the fragrance, preservative or other component which may be included and is not soluble in the aqueous carrier of the composition.

Alkylene glycols suitable for use in the described aerosol odor eliminating compositions include mono-, di- or tri-alkylene glycols, such as for example triethylene glycol, propylene glycol, dipropylene glycol, and mixtures thereof. A preferred mixture is about 0.1 to about 3.0 wt. % triethylene glycol and about 0.1 to about 3.0 wt. % propylene glycol.

As to the surfactant, the at least one surfactant is included in the odor eliminating composition in an amount of about 0.1 to about 4 wt. % of the composition, preferably about 0.1 to about 2 wt. % and most preferably about 0.1 to about 1.0 wt. %. The surfactant serves as a solubilizer alone or in conjunction with the alkylene glycol component for the fragrance, preservative or other component which may be present which is not soluble in the aqueous carrier of the composition. The at least one surfactant includes one or more surfactants having a hydrophile-lipophile-balance (HLB) of about 7 to about 20, preferably about 9 to about 18 and most preferably about 12 to about 16. Surfactants otherwise suitable for use can be nonionic, anionic, amphoteric, cationic, or a combination thereof. Preferably, the surfactant is one or more nonionic surfactants having an HLB within the above described ranges.

Nonionic surfactants suitable for use in the described aerosol odor eliminating compositions include alkoxylated compounds such as, for example, fatty alcohol alkoxylates, alkoxylated polyol fatty acid esters; alkyl polyglucosides; alkanolamides, including fatty acid alkanolamides; fatty alcohol polyalkyleneglycol ethers; oxo-alcohol polyalkylene glycol ethers; alkylphenol polyalkylene glycol ethers; fatty alcohol poly-poly glycol ethers (e.g. ethylene oxide/propylene oxide adducts); and alkyl dimethyl amine oxide, as well as nonionic polymers such as for example ethylene oxide/propylene oxide block copolymers. The alkoxy component is preferably ethoxy.

Specific preferred examples of nonionic surfactants suitable for inclusion are alkyloxypolyethyleneoxyethanol, such as the secondary $C_6$-$C_{17}$ alcohol ethoxylates with 3-6 ethylene oxide units; hydrogenated castor oil ethoxylate; octylphenol ethoxylate; alkyl polyglucoside; polyethylene glycol cocoamine; and the like.

Anionic surfactants suitable for use include soaps, alkyl benzene sulfonates, alkane sulfonates, α-olefin sulfonates; α-sulfo fatty acid methyl esters; fatty alcohol sulfates or alkyl sulfates; alkyl ether sulfates including fatty alcohol ether sulfates and oxo-alcohol ether sulfates; and the like, as well as combinations thereof.

Amphoteric surfactants suitable for use include alkyl betaines, alkyl sulfo betaines and the like, as well as combinations thereof.

Cationic surfactants suitable for use include tetraalkyl ammonium chlorides, and the like, as well as combinations thereof.

As to the compressed gas propellant, the compressed gas is included in an amount of about 0.1 to about 5 wt. %, preferably about 0.1 to about 3.5 wt. %, and most preferably about 0.1 to about 1.0 wt. %. The compressed gas propellant is useful in the stated amounts for providing a suitable particle size and spray rate over the life of the product when the pressure within the container is sufficient to provide an acceptable spray. The initial pressure of the container can be in a range of about 130 to about 180 psig at room temperature. The pressure will drop at a linear rate over the life of the product. However, the compositions of the invention will have a substantially consistent particle size and spray rate for at least about 70 to about 75% of the life of the aerosol. This higher pressure leads to improved break-up of aerosol particles which results in smaller sized droplets. The particle size is preferably within the conventional and accepted range for compressed gases, e.g. about 60-80 microns for the majority of the life of the product (i.e., about 100 to about 50% of the product life) and about 90-100 microns at the end of product life (i.e., about 50 to about 10% of the product life).

Compressed gases suitable for inclusion in the aerosol odor elimination composition are, for example, nitrogen, air, carbon dioxide, nitrous oxide, inert gases, and mixtures thereof. The propellants useful in the present invention are non-hydrocarbons.

As to the buffering system of the compositions, the buffering system is includable in an amount of about 0.01 to about 5 wt. %, preferably about 0.1 to about 3.0 wt. % and, most preferably, about 0.1 to about 1.0 wt. % of the composition. The buffering system in a preferred embodiment is composed of citric acid alone, a citrate compound alone, or a combination of citric acid and a citrate compound. This citric acid and/or citrate buffering system provides the desired buffering while remaining stable over an extended period of time and not providing any color change to the underlying composition. The stability is important to provide for an extended shelf or storage life for the composition.

Alternate buffering components may also be utilized in the buffering system, either in combination with the citric acid and/or citrate compound described above, as well as either or alone or in combination. Examples of such alternate components include alkali metal phosphate compounds such as dipotassium hydrogen phosphate and/or potassium dihydrogen phosphate; alkali metal bicarbonate, e.g., sodium bicarbonate; and alkali metal hydroxide, e.g. sodium hydroxide.

As to the fragrance component of the aerosol odor eliminating composition, the fragrance is includable in an amount that is sufficient to deliver a pleasant smell that can be perceived by a consumer and that treats at least a substantial portion of an airborne malodor. The fragrance is preferably present in an amount that not only completely masks airborne malodors, but also delivers a pleasant smell to be perceived by a consumer. In one embodiment, the fragrance is present in an amount ranging from about 0.01 to about 10 wt. %, more preferably from about 0.01 to about 5 wt. %, and most preferably from about 0.01 to about 3 wt. %.

Fragrances normally are composed of a mixture of a number of fragrant materials, each of which has a particular fragrant sense. The number of fragrant materials in a fragrance is typically ten or more. The range of fragrant materials used may vary. The materials come from a variety of chemical classes, but in general are water-insoluble oils. In many instances, the molecular weight of a fragrance material is in excess of 150, but does not exceed 300.

The fragrance may comprise one or more fragrant materials or materials that provide chemically active vapors. In one embodiment, the fragrance can comprise and/or include volatile, fragrant compounds including, but not limited to natural botanic extracts, essences, fragrance oils, synthetic fragrant materials and so forth. As is known in the art, many essential oils and other natural plant derivatives contain large percentages of highly volatile scents. In this regard, numerous essential oils, essences, and scented concentrates are commonly available from companies in the fragrance and food businesses. Exemplary oils and extracts include, but are not limited to, those derived from the following plants: almond, amyris, anise, armoise, bergamot, cabreuva, calendula, canaga, cedar, chamomile, coconut, eucalyptus, fennel, jasmine, juniper, lavender, lemon, orange, palm, peppermint, quassia, rosemary, thyme, and so forth. The fragrant materials are considered the "active" component of the fragrance. The fragrance may or may not include a carrier for the fragrant material.

The aerosol elimination compositions are aqueous based. Accordingly, water is present in a balance amount to equal 100% when combined with the other components making up the total composition. The water can be reverse osmosis (RO) water, deionized water, tap water, or the like. Preferably, RO water is utilized.

The volatile organic content (VOC) of the total composition is less than 5.0% based on 100 wt. % of the components of the composition, preferably less than 3.0% and most preferably less than 1.0%, and further less than 0.5%. Alternatively, the VOC of the total composition based on 100 wt. % in absence of the wt. % of the active fragrant material is less than 0.1%, preferably less than 0.05% and, most preferably, less than 0.01%.

The pH of the composition is from about 4 to about 8, preferably about 5 to about 7.

Generally fragrances are pH dependent, can discolor the composition to which they are added and can disrupt the stability of the composition to which they are added. Accordingly, it is important to solubilize the fragrance component to render the composition stable. Water-based systems are problematic for solubilizing a fragrance since fragrances generally are present partially or totally as an oil. In the past, solubilization has been provided with a volatile solvent such as ethanol, which necessarily results in a higher VOC in the composition. In the aerosol eliminating composition, a volatile solvent for solubilizing the fragrance is not provided. Rather, solubilization of the fragrance is provided by the at least one nonionic surfactant and/or the at least one alkylene glycol. Thus, the VOC of the composition is maintained at a low level. No alcohol or other volatile solvent is present in the aerosol elimination composition of the invention. The VOC of the composition is thus essentially based on that of the fragrance component and any additive component, e.g. a preservative, which may contain a volatile ingredient. Other additives as known for inclusion in an aerosol odor treating composition are also includable in the compositions described herein to the extent they conform to the limitations described herein.

The spray dispenser including a base container and spray head with valve and actuator can be constructed of any conventional material. The container is preferably aluminum and the spray head is preferably all or substantially all plastic. The container is capable of withstanding internal pressure of from about 130 to about 180 psig at room temperature. The spray head is constructed necessarily to disperse the contents of the container in the form of a spray of fine or finely divided particles or droplets. As set forth above, a conventional and accepted range of particle sizes for compressed gas aerosols is about 60 to about 80 microns over the substantial majority of the life of the container (i.e., about 100 to about 50% of the life) and about 90-100 microns at the end of the life of the container (i.e., about 50 to about 10% of the life).

The average spray rate of the aerosol odor eliminating composition upon dispensing is in the general range of about 0.5 to about 2.5 g/sec, mid-range of about 0.75 to 2.25 g/sec and a preferred range of about 1 to about 2 grams/second (g/sec), more preferably about 1.1 to about 1.9 g/sec and most preferably about 1.2 to about 1.8 g/sec. The average spray rate is determined by providing an aerosol composition sample and pressurizing to various elevated pressures to insure acceptable spray performance at the higher end of possible ranges. A specific example is to provide three groups of six identical samples and pressurizing with nitrogen gas to 150 psig, 160 psig and 170 psig and spray test each sample using a Malvern Masterizer S volume-based particle analyzer. The Malvern analyzer obtains a Sauter mean diameter (SMD), defined as the ratio of the volume diameter, and the mass median diameter (MMD) for a particle diameter which 10%, 50% and 90% of the volume sampled is below the measured particle diameter. Test samples were sprayed down from a 100% full can to a 25% full can with data measurements taken at 100%, 75%, 50% and 25% intervals.

To illustrate the spray performance of a composition of the invention, a preferred composition is described below as is the spray testing to which the composition was subjected and the results of such spray testing. The results show that the spray rates are consistent over a varied pressure range.

Spray Rate Evaluation

The purpose of the tests described below is to evaluate the spray performance of aerosol odor elimination compositions using a standard container and a standard production Glencoe type actuator cap at elevated pressures of 150 psig, 160 psig and 170 psig. To obtain an acceptable spray pattern for a compressed gas aerosol, the actuator should contain a mechanical break-up unit (MBU). The function of the MBU is to break up the liquid product as it is dispensed from the container. Compositions of the invention provide for improved spray in various aspects as described herein based on the make-up of the composition itself as opposed to a particular actuator structure. However, the spray performance of the present described compositions can be maximized by varying one or more internal mechanisms of the MBU. Such mechanisms include, for example, the orifice diameter (which preferably is between about 0.010" to about 0.015" for room sprays), orifice land length, spin chamber diameter, spin chamber depth, number of channels (tangential), channel depth, channel width and the like.

The spray testing was conducted on aerosol samples having the composition set forth below that were pressurized to various elevated pressures to insure acceptable spray performance at the higher end of possible pressure ranges. Samples were built with Seaquist actuators (Ref. #GL000158, Model DU3020 which has an orifice diameter of 0.012".). Three groups of six samples were pressurized with $N_2$ to 150 psig, 160 psig and 170 psig were spray tested using a Malvern Masterizer S volume based particle analyzer. The Malvern analyzer obtained the Sauter mean diameter (SMD), defined as the ratio of the volume diameter and the surface area diameter, and the mass median diameter (MMD) for a particle diameter which 10%, 50% and 90% of the volume sampled is below the measured particle diameter. Test samples were sprayed down from 100% full can to 25% full can with four data measurements taken at 100%, 75%, 50% and 25% intervals. Spray rates were also calculated independent of the Malvern analyzer using a stop watch and analytical balance to confirm measurements.

As shown in FIG. 1, the spray down rates of each pressure group (i.e., 170 psig, 160 psig and 150 psig) were very close when compared to each other and were within about 0.1 gram/second at each spray interval. Spray testing results for particle size (see FIG. 2) also indicated the particle mass median diameters (MMD) at 50% to be consistently close when compared to each pressure group and within about 5 μm at each data point during the spray down.

Figure 2:
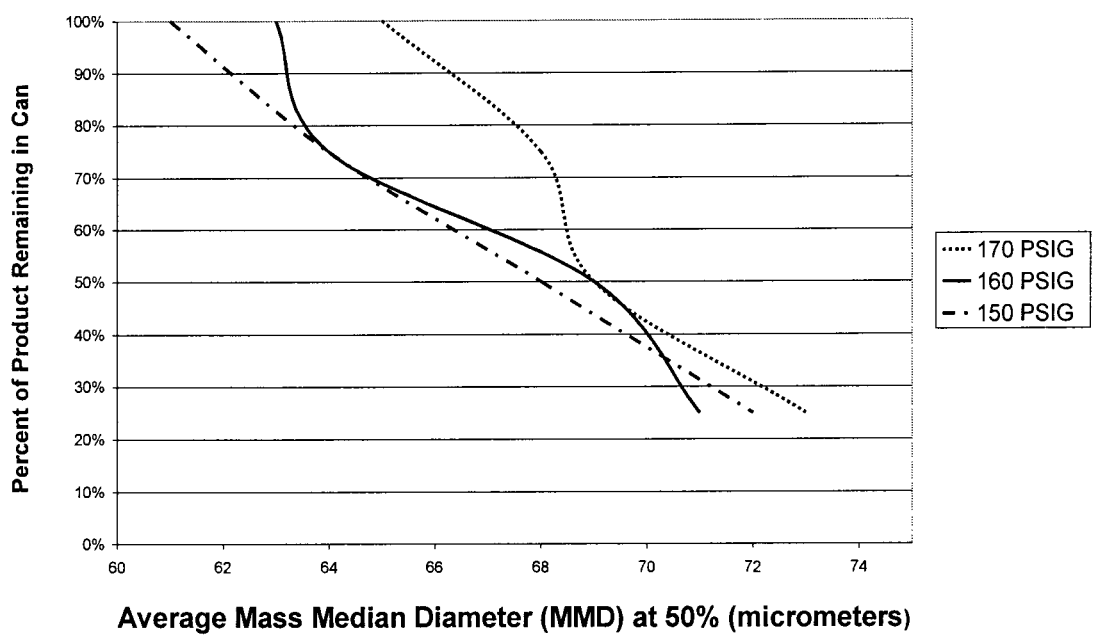
FIG. 2 shows graphically the average mass median diameter (MMD) of particles for samples evaluated at 170, 160 and 150 psig.

The spray test results are shown below in Tables 1, 2 and 3 and in FIGS. 1 and 2 for six test units pressurized to 170 psig, 160 psig and 150 psig respectively. The contents from test samples were collected and analyzed for pH. The measured pH was 7.3. The composition formula was as follows:

Test Composition 1 (Invention)

| Component | Wt. % |
|---|---|
| Reverse Osmosis Water | 95.93 |
| Triethylene Glycol (98%) | 1.0 |
| Nitrogen Gas | 0.68 |
| Propylene Glycol | 0.5 |
| Fragrance | 0.5 |
| Hydrogenated Castor Oil 60 Ethoxylate | 0.47 |
| Dipotassium Hydrogen Phosphate | 0.32 |
| Secondary $C_6$-$C_{17}$ Alcohol Ethoxylate (3-6 EO) | 0.28 |
| Potassium Dihydrogen Phosphate | 0.17 |
| Preservative* | 0.15 |
|  | 100% |

*2-methyl-4-isothiazolin-3-one.

TABLE 1

Spray test results for 170 psig samples

| 170 PSIG | Sample# | Sauter Mean Diameter (μm) | MMD 10% (μm) | MMD 50% (μm) | MMD 90% (μm) | Spray Rate (gm/sec.) |
|---|---|---|---|---|---|---|
| 100% Full Can | 1 | 41.13 | 25.08 | 55.94 | 104.05 | 1.83 |
| | 2 | 55.10 | 32.99 | 67.75 | 120.07 | 1.99 |
| | 3 | 51.58 | 30.61 | 67.83 | 112.42 | 2.03 |
| | 4 | 54.14 | 34.91 | 66.44 | 107.93 | 1.75 |
| | 5 | 52.21 | 31.78 | 66.44 | 111.59 | 1.79 |
| | 6 | 52.48 | 31.82 | 64.62 | 109.32 | 1.70 |
| | Average | 51 | 31 | 65 | 111 | 1.85 |
| 75% Full Can | 1 | 43.53 | 26.98 | 56.86 | 102.38 | 1.46 |
| | 2 | 52.30 | 33.99 | 68.93 | 113.42 | 1.51 |
| | 3 | 50.04 | 33.09 | 67.83 | 114.00 | 1.54 |
| | 4 | 58.53 | 42.26 | 73.61 | 113.19 | 1.47 |
| | 5 | 59.34 | 38.36 | 71.98 | 114.82 | 1.44 |
| | 6 | 49.11 | 34.64 | 66.16 | 110.12 | 1.35 |
| | Average | 52 | 35 | 68 | 111 | 1.46 |
| 50% Full Can | 1 | 49.33 | 29.66 | 59.20 | 103.52 | 1.34 |
| | 2 | 51.66 | 32.53 | 61.89 | 110.33 | 1.35 |
| | 3 | 58.20 | 34.80 | 71.57 | 122.09 | 1.32 |
| | 4 | 70.01 | 46.25 | 78.87 | 119.32 | 1.27 |
| | 5 | 58.62 | 39.86 | 71.75 | 116.94 | 1.24 |
| | 6 | 56.59 | 34.51 | 68.22 | 113.36 | 1.20 |
| | Average | 57 | 36 | 69 | 114 | 1.29 |
| 25% Full Can | 1 | 53.52 | 31.41 | 64.69 | 117.69 | 1.20 |
| | 2 | 59.58 | 36.03 | 70.51 | 122.17 | 1.21 |
| | 3 | 62.67 | 37.58 | 76.88 | 127.47 | 1.20 |
| | 4 | 65.94 | 39.78 | 80.14 | 132.37 | 1.15 |
| | 5 | 61.36 | 37.09 | 74.22 | 126.70 | 1.10 |
| | 6 | 59.22 | 35.46 | 71.00 | 124.42 | 1.08 |
| | Average | 60 | 36 | 73 | 125 | 1.16 |

TABLE 2

Spray test results for 160 psig samples

| 160 PSIG | Sample# | Sauter Mean Diameter (μm) | MMD 10% (μm) | MMD 50% (μm) | MMD 90% (μm) | Spray Rate (gm/sec.) |
|---|---|---|---|---|---|---|
| 100% Full Can | 1 | 53.99 | 32.07 | 68.47 | 115.50 | 1.85 |
| | 2 | 49.11 | 29.62 | 60.64 | 102.58 | 1.68 |
| | 3 | 43.82 | 29.89 | 62.92 | 110.86 | 1.88 |
| | 4 | 48.94 | 28.81 | 62.49 | 112.59 | 1.83 |
| | 5 | 47.36 | 31.15 | 60.60 | 102.74 | 1.78 |
| | 6 | 52.42 | 33.62 | 64.32 | 104.82 | 1.77 |
| | Average | 49 | 31 | 63 | 108 | 1.80 |
| 75% Full Can | 1 | 45.11 | 28.58 | 58.11 | 108.07 | 1.37 |
| | 2 | 51.97 | 31.06 | 63.44 | 108.69 | 1.41 |
| | 3 | 54.35 | 36.75 | 70.81 | 115.34 | 1.55 |
| | 4 | 51.88 | 31.68 | 64.70 | 111.58 | 1.54 |
| | 5 | 48.24 | 31.30 | 62.76 | 107.82 | 1.47 |
| | 6 | 53.20 | 38.84 | 66.88 | 105.44 | 1.46 |
| | Average | 51 | 33 | 64 | 109 | 1.47 |
| 50% Full Can | 1 | 53.01 | 31.16 | 64.11 | 111.65 | 1.15 |
| | 2 | 59.13 | 37.04 | 68.52 | 109.67 | 1.22 |
| | 3 | 63.04 | 40.62 | 73.88 | 117.56 | 1.36 |
| | 4 | 56.05 | 33.76 | 68.36 | 116.39 | 1.39 |
| | 5 | 57.30 | 35.60 | 69.64 | 114.97 | 1.30 |
| | 6 | 60.03 | 37.48 | 72.35 | 116.41 | 1.29 |
| | Average | 58 | 36 | 69 | 114 | 1.28 |
| 25% Full Can | 1 | 55.47 | 32.97 | 66.37 | 114.49 | 1.02 |
| | 2 | 55.36 | 31.68 | 68.04 | 120.27 | 1.09 |
| | 3 | 63.34 | 39.06 | 74.98 | 129.32 | 1.20 |
| | 4 | 57.30 | 33.35 | 69.54 | 125.59 | 1.20 |
| | 5 | 52.03 | 33.39 | 73.39 | 140.37 | 1.16 |
| | 6 | 60.83 | 36.94 | 72.82 | 124.75 | 1.16 |
| | Average | 57 | 35 | 71 | 126 | 1.14 |

TABLE 3

Spray test results for 150 psig samples

| 150 PSIG | Sample# | Sauter Mean Diameter (μm) | MMD 10% (μm) | MMD 50% (μm) | MMD 90% (μm) | Spray Rate (gm/sec.) |
|---|---|---|---|---|---|---|
| 100% Full Can | 1 | 55.06 | 32.95 | 70.26 | 118.74 | 1.75 |
| | 2 | 49.47 | 29.43 | 64.08 | 109.32 | 1.66 |
| | 3 | 40.65 | 25.52 | 56.28 | 96.13 | 1.67 |
| | 4 | 44.59 | 28.59 | 61.32 | 107.16 | 1.84 |
| | 5 | 43.77 | 27.37 | 58.48 | 102.22 | 1.67 |
| | 6 | 42.03 | 27.65 | 57.42 | 96.37 | 1.67 |
| | Average | 46 | 29 | 61 | 105 | 1.71 |
| 75% Full Can | 1 | 56.66 | 33.65 | 71.47 | 122.32 | 1.46 |
| | 2 | 45.50 | 27.92 | 61.03 | 108.45 | 1.42 |
| | 3 | 41.42 | 28.54 | 61.64 | 107.13 | 1.45 |
| | 4 | 50.28 | 31.07 | 62.05 | 106.95 | 1.49 |
| | 5 | 49.75 | 33.04 | 63.47 | 106.70 | 1.43 |
| | 6 | 44.91 | 28.74 | 62.33 | 108.04 | 1.41 |
| | Average | 48 | 30 | 64 | 110 | 1.44 |
| 50% Full Can | 1 | 59.89 | 36.27 | 72.51 | 119.28 | 1.35 |
| | 2 | 52.94 | 31.55 | 65.09 | 113.06 | 1.26 |
| | 3 | 53.89 | 32.27 | 66.37 | 113.24 | 1.25 |
| | 4 | 56.59 | 35.63 | 66.59 | 112.11 | 1.31 |
| | 5 | 56.52 | 35.38 | 66.53 | 111.51 | 1.20 |
| | 6 | 59.72 | 37.56 | 70.67 | 112.96 | 1.25 |
| | Average | 57 | 35 | 68 | 114 | 1.27 |
| 25% Full Can | 1 | 62.02 | 36.56 | 75.18 | 132.59 | 1.21 |
| | 2 | 59.49 | 35.01 | 72.38 | 130.01 | 1.11 |
| | 3 | 56.89 | 33.94 | 69.87 | 121.31 | 1.14 |
| | 4 | 58.33 | 35.04 | 69.53 | 122.98 | 1.16 |
| | 5 | 59.15 | 35.22 | 71.06 | 124.43 | 1.05 |
| | 6 | 59.01 | 35.06 | 72.21 | 124.22 | 1.10 |
| | Average | 59 | 35 | 72 | 126 | 1.13 |

To illustrate spray rate consistency at the low end of tolerances, i.e., compositions pressurized at 133 psig, four inventive compositions were tested as set forth below together with the test results in Table 4.

Test Composition 1—As described above.

| Components | Wt. % Test Composition 2 | Wt. % Test Composition 3 | Wt. % Test Composition 4 |
|---|---|---|---|
| Reverse Osmosis Water | 95.83 | 96.85 | 96.95 |
| Citric Acid (50%) | 0.3 | 0.3 | 0 |
| Sodium Citrate Dihydrate | 0.3 | 0.3 | 0 |
| Triethylene Glycol 98%) | 1.0 | 0 | 0 |
| Hydrogenated Castor Oil 60 Ethoxylate | 0.46 | 0.47 | 0.47 |
| Secondary $C_6$-$C_{17}$ Alcohol Ethoxylate | 0.28 | 0.28 | 0.28 |
| Fragrance | 0.5 | 0.5 | 0.5 |
| Propylene Glycol | 0.5 | 0.47 | 0.47 |
| Preservative* | 0.15 | 0.15 | 0.15 |
| Nitrogen Gas | 0.68 | 0.68 | 0.68 |
| Dipotassium Hydrogen Phosphate | 0 | 0 | 0.33 |
| Potassium Dihydrogen Phosphate | 0 | 0 | 0.17 |
|  | 100% | 100% | 100% |

*2-methyl-isothiazolin-3-one

TABLE 4

Spray Rate Test

| Comp.#/ Sample# | Initial Wt. (g) | Final Wt. (g) | Difference (g) | Spray rate (g/s) |
|---|---|---|---|---|
| 1-1 | 340.80 | 258.27 | 82.53 | 1.38 |
| 1-2 | 341.00 | 260.36 | 80.64 | 1.34 |
| 1-3 | 343.90 | 266.44 | 77.46 | 1.29 |
| 1-4 | 343.63 | 263.15 | 80.48 | 1.34 |
| 1-5 | 340.13 | 268.13 | 72.00 | 1.20 |
| 1-6 | 339.52 | 265.62 | 73.90 | 1.23 |
|  |  |  | Average = | 1.30 |
|  |  |  | STD DEV = | 0.07 |
| 2-1 | 339.61 | 258.66 | 80.95 | 1.35 |
| 2-2 | 339.84 | 258.31 | 81.53 | 1.36 |
| 2-3 | 339.36 | 257.28 | 82.08 | 1.37 |
| 2-4 | 340.01 | 266.16 | 73.85 | 1.23 |
| 2-5 | 342.68 | 265.59 | 77.09 | 1.28 |
| 2-6 | 342.96 | 265.53 | 77.43 | 1.29 |
|  |  |  | Average = | 1.31 |
|  |  |  | STD DEV = | 0.05 |
| 3-1 | 343.07 | 268.98 | 74.09 | 1.23 |
| 3-2 | 341.00 | 265.57 | 75.43 | 1.26 |
| 3-3 | 341.91 | 261.35 | 80.56 | 1.34 |
| 3-4 | 341.23 | 263.62 | 77.61 | 1.29 |
| 3-5 | 341.27 | 264.04 | 77.23 | 1.29 |
| 3-6 | 331.59 | 249.12 | 82.47 | 1.37 |
|  |  |  | Average = | 1.30 |
|  |  |  | STD DEV = | 0.05 |
| 4-1 | 341.40 | 267.45 | 73.95 | 1.23 |
| 4-2 | 340.73 | 262.23 | 78.50 | 1.31 |
| 4-3 | 340.85 | 262.86 | 77.99 | 1.30 |
| 4-4 | 343.41 | 258.85 | 84.56 | 1.41 |
| 4-5 | 344.12 | 271.14 | 72.98 | 1.22 |
| 4-6 | 342.61 | 265.61 | 77.00 | 1.28 |
|  |  |  | Average = | 1.29 |
|  |  |  | STD DEV = | 0.07 |

A sensory evaluation was also conducted with regard to Test Composition 3 and a commercially available air spray as sold under the name "Febreze® Air Effects®" Spring & Renewal™ as sold by The Procter & Gamble Company. The evaluation was to determine on a comparison basis the intensity of the fragrance over time.

The test method used a Trained Intensity Panel (19 panelists per test session present in a 800 cubic foot room. Panelists entered the room in small groups (4-5 people per group). The panelists evaluated the pair of products. Three 2-product randomizations were used for the testing. To learn fragrance longevity, the products were each disposed as a 4 gram dose with no refreshing. The evaluations were at every 10 minutes beginning at 5 minutes after the initial treatment through 45 minutes.) The fragrance was rated at 10 minute intervals on a scale of from 0 to 7 with 7 being the highest intensity, and the ratings then averaged to provide a fragrance intensity rating number. The fragrance ratings for the test samples are set forth in Table 5 below and shown graphically in FIG. 3.

TABLE 5

| Sample | Time |  |  |  |  |  |
|---|---|---|---|---|---|---|
|  | 5 Min. | 15 Min. | 25 Min. | 35 Min. | 45 Min. | 55 Min. |
| Febreze ® Spring & Renewal ™ | 6.3 | 5.9 | 4.9 | 4.5 | 3.8 | 2.9 |
| Test Composition 3 | 6.8 | 6.3 | 5.3 | 4.5 | 4.0 | 3.5 |

Figure 3:
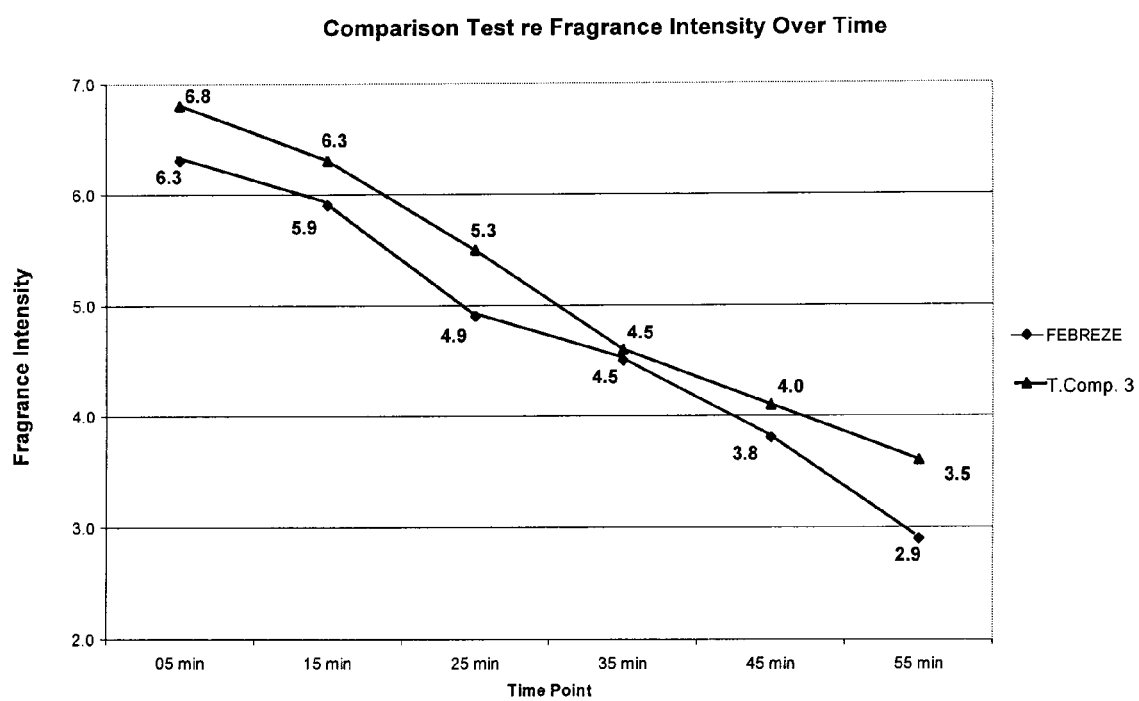
FIG. 3 shows graphically the results of a comparison test as to fragrance intensity over time.

Both compositions decreased in intensity at the same rate. Directionally, as shown in FIG. 3, the Febreze® composition is lower than Test Composition 3 of the invention.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. An aerosol article for treating malodors comprising
(1) a dispensing container including a spray head and (2) a composition for dispensing from said container; wherein said composition based on a 100 wt. % comprises
   (a) about 0.01 to about 10 wt. % of at least one fragrance component,
   (b) about 0.1 to about 5 wt. % of a compressed gas propellant,
   (c) about 0.01 to about 5 wt. % of a buffering system,
   (d) about 0.1 to about 10 wt. % of at least one alkylene glycol,
   (e) about 0.1 to about 4 wt. % of at least one surfactant, wherein one or more of said at least one surfactant has a hydrophile-lipophile-balance (HLB) of about 7 to about 20,
   (f) optionally, at least one adjuvant selected from the group consisting of preservatives, antimicrobials, corrosion inhibitors, and pH adjusters, and
   (g) a balance of water; and
wherein said composition is (i) a single phase composition, (ii) has a volatile organic content of less than 5.0% based on 100 wt. % of the composition, and (iii) does not contain any low molecular weight monohydric alcohol; and wherein pressure of the container is initially in a range of about 130 to about 180 psig at room temperature and drops at a linear rate over life of the composition, and said composition is dispensed from said container at a spray rate of about 0.5 g/sec to about 2.5 g/sec as aerosol particles having particle mass median diameters of about 60 to about 80 microns for 100% to about 50% of life of the composition and particle mass median diameters of about 90 to about 100 microns over about 50% to about 10% of the life of the composition.

2. The aerosol article of claim 1, wherein said at least one alkylene glycol is present in an amount of about 0.1 to about 5 wt. %.

3. The aerosol article of claim 1, wherein said at least one alkylene glycol is present in an amount of about 0.5 to about 1.5 wt. %.

4. The aerosol article of claim 1, wherein said at least one alkylene glycol is propylene glycol, or triethylene glycol, or propylene glycol and triethylene glycol.

5. The aerosol article of claim 1, wherein said compressed gas propellant is present in an amount of about 0.1 to about 3.5 wt. %.

6. The aerosol article of claim 1, wherein said buffering system is citric acid, a citrate compound, or a combination of citric acid and a citrate compound.

7. The aerosol article of claim 1, wherein said buffering system is citric acid and at least one of alkali metal citrate, dipotassium hydrogen phosphate, potassium dihydrogen phosphate, sodium bicarbonate and alkali metal hydroxide.

8. The aerosol article of claim 1, wherein said buffering system is citric acid and sodium citrate.

9. The aerosol article of claim 1, wherein said buffering system is citric acid and dipotassium hydrogen phosphate.

10. The aerosol article of claim 1, wherein said buffering system is dipotassium hydrogen phosphate and potassium dihydrogen phosphate.

11. The aerosol article of claim 1, wherein the HLB is of about 9 to about 18.

12. The aerosol article of claim 1, wherein the HLB is of about 12 to about 16.

13. The aerosol article of claim 1, wherein said at least one nonionic surfactant is a hydrogenated castor oil ethoxylate and a secondary alcohol ethoxylate.

14. The aerosol article of claim 1, wherein said compressed gas propellant is nitrogen, air, nitrous oxide, carbon dioxide, inert gases, or a mixture thereof.

15. The aerosol article of claim 1, wherein said at least one alkylene glycol includes about 0.1 to about 3.0 wt. % triethylene glycol and about 0.1 to about 3.0 wt. % propylene glycol.

16. The aerosol article of claim 1 further comprising a preservative.

17. The aerosol article of claim 1, wherein said spray rate is about 0.75 to about 2.25 g/sec.

18. The aerosol article of claim 1, wherein said spray rate is about 1 to about 2 g/sec.

19. The aerosol article of claim 1, wherein said spray rate is about 1.1 to about 1.9 g/sec.

20. The aerosol article of claim 1, wherein said spray rate is about 1.2 to about 1.8 g/sec.

* * * * *